(12) United States Patent
Kubota (10) Patent No.: US 8,981,300 B2
(45) Date of Patent: Mar. 17, 2015

(54) ELECTROMAGNETIC WAVE PULSE MEASURING DEVICE AND METHOD, AND APPLICATION DEVICE USING THE SAME

(71) Applicant: Canon Kabushiki Kaisha, Tokyo (JP)

(72) Inventor: Oichi Kubota, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/375,374

(22) PCT Filed: Mar. 13, 2013

(86) PCT No.: PCT/JP2013/058175
§ 371 (c)(1),
(2) Date: Jul. 29, 2014

(87) PCT Pub. No.: WO2013/141326
PCT Pub. Date: Sep. 26, 2013

(65) Prior Publication Data
US 2015/0008326 A1  Jan. 8, 2015

(30) Foreign Application Priority Data

Mar. 19, 2012  (JP) ................................ 2012-061391

(51) Int. Cl.
*G01N 21/00* (2006.01)
*G01N 21/3586* (2014.01)
*G01N 29/07* (2006.01)

(52) U.S. Cl.
CPC ............ *G01N 21/3586* (2013.01); *G01N 29/07* (2013.01); *G01N 2291/011* (2013.01);
(Continued)

(58) Field of Classification Search
USPC ..................... 250/336.1, 338.1, 339.07, 341.1
See application file for complete search history.

(56) References Cited

U.S. PATENT DOCUMENTS

2003/0149346 A1  8/2003  Arnone et al.
2006/0027021 A1  2/2006  Choi et al.
(Continued)

FOREIGN PATENT DOCUMENTS

JP   2003-525447 A   8/2003
JP   2007-216001 A   8/2007
(Continued)

OTHER PUBLICATIONS

Dekorsy, T., et al., "Coherent acoustic phonons in nanostructures investiaged by asynchronous optical sampling," Proc. of SPIE, vol. 6393 (2006)—11 pages.

(Continued)

*Primary Examiner* — Mark R Gaworecki
(74) *Attorney, Agent, or Firm* — Fitzpatrick, Cella, Harper & Scinto (57) ABSTRACT

An electromagnetic wave pulse measuring device, includes an elastic vibration wave generating section which irradiates a predetermined area of a sample with an elastic vibration wave, an electromagnetic wave pulse generating section which irradiates the predetermined area, which is irradiated with the elastic vibration wave, with an electromagnetic wave pulse, and an electromagnetic wave pulse detecting section which measures a waveform of the electromagnetic wave pulse modulated in the predetermined area by the elastic vibration wave. The timing at which the electromagnetic wave pulse detecting section measures the waveform of the electromagnetic wave pulse is a timing at which a phase angle of the elastic vibration wave has a predetermined value when the elastic vibration wave generating section generates the elastic vibration wave.

12 Claims, 10 Drawing Sheets

(52) U.S. Cl.
CPC ...... *G01N2291/023* (2013.01); *G01N 2291/10* (2013.01); *G01N 2201/0697* (2013.01); *G01N 2201/06113* (2013.01); *G01N 2201/067* (2013.01)
USPC .................................. 250/341.1; 250/338.1

(56) References Cited

U.S. PATENT DOCUMENTS

| | | |
|---|---|---|
| 2009/0156932 A1 | 6/2009 | Zharov |
| 2011/0021907 A1 | 1/2011 | Igarashi |
| 2013/0060122 A1 | 3/2013 | Zharov |

FOREIGN PATENT DOCUMENTS

| | | |
|---|---|---|
| JP | 2008-168038 A | 7/2008 |
| JP | 4603100 B2 | 12/2010 |
| WO | 01/65240 A1 | 9/2001 |
| WO | 2010/095487 A1 | 8/2010 |

OTHER PUBLICATIONS

International Search Report and Written Opinion of the International Searching Authority issued in counterpart application No. PCT/JP2013/058175 dated Jun. 24, 2013—11 pages.

International Preliminary Report on Patentability in International Application No. PCT/JP2013/058175, mailed Oct. 2, 2014.

FIG. 3A BEFORE SOUND WAVE IRRADIATION

FIG. 3B DURING SOUND WAVE IRRADIATION

ELECTROMAGNETIC WAVE PULSE MEASURING DEVICE AND METHOD, AND APPLICATION DEVICE USING THE SAME

TECHNICAL FIELD

The present invention relates to an electromagnetic wave pulse measuring device and method for irradiating a target (sample) with an electromagnetic wave pulse and an elastic vibration wave such as a sound wave, analyzing the obtained electromagnetic wave pulse, and acquiring information on the target (typically, time-domain spectroscopy is used as a method of receiving the electromagnetic wave pulse) and relates to a tomography device and the like using the same.

BACKGROUND ART

In recent years, various testing techniques using an electromagnetic wave whose frequency ranges from 30 GHz to 30 THz, which is a so-called terahertz wave, have been developed. Nondestructive testing using transparency and spectroscopy using that biomolecules have characteristic absorption in the terahertz band are the examples of the aforementioned testing techniques. An imaging device which obtains a tomographic image by analyzing a detected terahertz wave has been developed, too.

In the example described in Japanese Unexamined Patent Application Publication (Translation of PCT Application) No. 2003-525447, assuming that an ultrashort pulsed laser beam is a pump light, an electromagnetic wave pulse having a frequency in the terahertz domain is generated and then a sample is irradiated with the electromagnetic wave pulse. The electromagnetic wave pulse which was reflected on or passed through the sample is detected by time-domain spectroscopy (TDS method) with the aforementioned pump light, a detector, and an optical delay system. In the TDS method in which the waveform itself of the electromagnetic wave pulse is observed, the amplitude and phase of an electric field are acquired at a time. In other words, the method is characterized by that information on both of the real part and the imaginary part of a complex index of refraction is able to be acquired at a time.

Meanwhile, with respect to a nondestructive testing method using visible to infrared light which is easy to deal with or a sound wave which is an elastic vibration wave (particularly, an ultrasonic wave having a frequency exceeding an audible range), conventionally, numerous methods have been developed and used. Like a tissue in a biological body, in the case of low contrast between a focused region and its surrounding, a method with a combination of light and an ultrasonic wave is used, too. In examples described in Japanese Patent Application Laid-Open No. 2007-216001 and Japanese Patent No. 4603100, a region of a sample required to be tested is irradiated with both of a laser beam and an ultrasonic wave. The ultrasonic wave modulates the density and the refractive index of the sample. Therefore, the intensity and the phase of the laser beam, which passed through or was reflected on the sample, are also affected by the ultrasonic wave. Laser beam variations, which occurred as a result, reflect the characteristics of the irradiated region. Therefore, the distribution of characteristics of the sample can be obtained by performing measurement while changing the position of the sample irradiated with the light and the ultrasonic wave.

SUMMARY OF INVENTION

Technical Problem

In the method in Japanese Unexamined Patent Application Publication (Translation of PCT Application) No. 2003-525447, however, it is possible that the signal contrast cannot be sufficiently secured in the case of a slight difference in refractive index or the case of a gradual and moderate change even if there is a difference in the region of the sample to be observed. In addition, if there is such a situation in the depth direction in a catoptric system, information may not be able to be obtained because an electromagnetic wave pulse does not return.

Moreover, in the method described in Japanese Patent Application Laid-Open No. 2007-216001 or in Japanese Patent No. 4603100, a change in the refractive index of the sample generated along with the ultrasonic wave irradiation is acquired from a change in the phase of the irradiation light which is a continuous light. Since it is only required that there is a difference in at least one of the refractive index and the elastic compliance, the difference is very likely to be detected in comparison with a case of using only either one of the light and the ultrasonic wave. Note that, however, information obtained by measurement at respective points here is limited to a change in the phase of the irradiation light, namely information on a real part of the refractive index.

Solution to Problem

Therefore, according to one aspect of the present invention, there is provided an electromagnetic wave pulse measuring device, including: an elastic vibration wave generating section which irradiates a predetermined area of a sample with an elastic vibration wave; an electromagnetic wave pulse generating section which irradiates the predetermined area, which is irradiated with the elastic vibration wave, with an electromagnetic wave pulse; and an electromagnetic wave pulse detecting section which measures a waveform of the electromagnetic wave pulse modulated in the predetermined area by the elastic vibration wave, wherein the timing at which the electromagnetic wave pulse detecting section measures the waveform of the electromagnetic wave pulse is a timing at which a phase angle of the elastic vibration wave has a predetermined value when the elastic vibration wave generating section generates the elastic vibration wave.

Further features of the present invention will become apparent from the following description of exemplary embodiments with reference to the attached drawings.

DESCRIPTION OF EMBODIMENTS

The present invention is characterized by that, in irradiating a predetermined area of a sample with a sound wave and an electromagnetic wave pulse and then measuring the waveform of the electromagnetic wave pulse modulated in the predetermined area by the sound wave, the timing of measuring the waveform of the electromagnetic wave pulse is a timing at which a phase angle of the sound wave at the sound wave oscillation has a predetermined value. Thereby, when the electromagnetic wave pulse is modulated in the predetermined area of the sample, the area is able to be irradiated with a sound wave having a certain phase angle, thus enabling a reliable measurement of the waveform of the electromagnetic wave pulse modulated in the area. In this process, for example, if the oscillation mode of the electromagnetic wave pulse is fixed in advance and the phase angle of the sound wave at the sound wave oscillation is scanned, the phase angle of the sound wave in the predetermined area is able to be changed. Therefore, the phase angle of the sound wave in the predetermined area is able to be set to a desired value by monitoring a change in the electromagnetic wave pulse modulated in the predetermined area by the sound wave while measuring the electromagnetic wave pulse. On the basis of the above way of thinking, an electromagnetic wave pulse measuring device and a method thereof according to the present invention have the basic configuration as described above.

Figure 1:
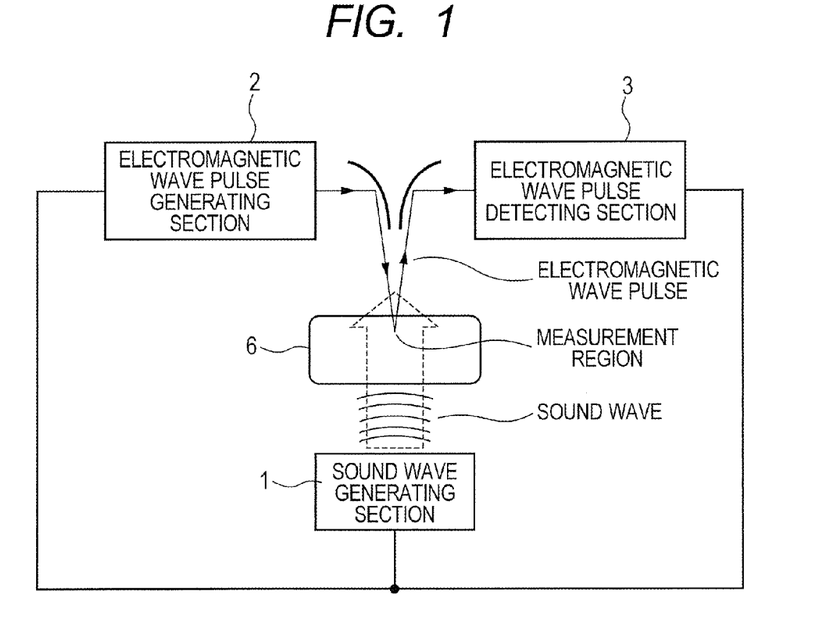
FIG. 1 is a block diagram illustrating a basic configuration of an electromagnetic wave pulse measuring device or method of the present invention.

Hereinafter, the features of the present invention will be described with reference to appended drawings and then the exemplary embodiments and examples of the present invention will be described. The features of the present invention will now be described. Referring to FIG. 1, there is illustrated a block diagram of a basic configuration of the present invention. A sound wave generating section (an elastic vibration wave generating section) 1 generates a sound wave toward a measurement region of a sample 6. An electromagnetic wave pulse generating section 2 generates a pulse of an electromagnetic wave which is present only for an extremely short period of time and irradiates the measurement region of the sample 6 with the electromagnetic wave pulse. The electromagnetic wave pulse modulated in the measurement region by an interaction with the sample comes out to the outside with the waveform changed. An electromagnetic wave pulse detecting section 3 captures the electromagnetic wave pulses including information on the measurement region and measures the waveforms of the electromagnetic wave pulses. In this manner, information on both of the amplitude and the phase of the pulse waveform is acquired. In other words, one of the features of the present invention is to perform time-domain spectroscopic measurement. In the present invention, so-called autocorrelation THz spectroscopy, in which a correlation is found in the electromagnetic wave pulse between during the irradiation of the sample and after the irradiation thereof, may be performed in addition to performing the time-domain spectroscopic measurement for the waveform of an electromagnetic wave pulse obtained from a sample by reflection or transmission by using an optical switch or an electro-optic effect (Pockels effect) and the like.

Figure 2A:
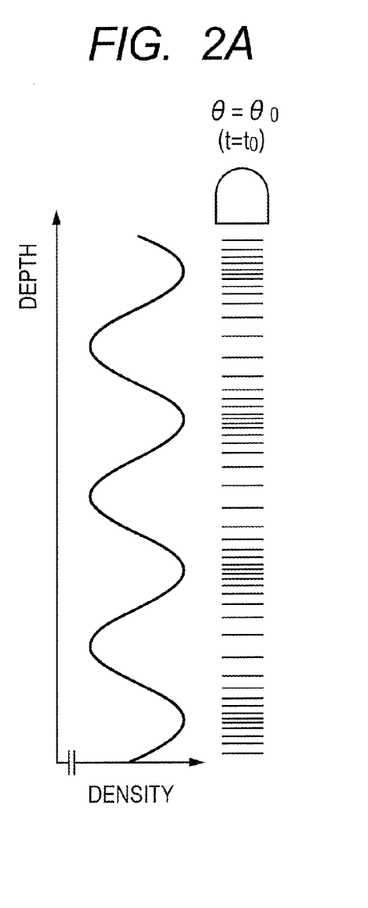
FIGS. 2A and 2B are diagrams illustrating the states in which a sample is irradiated with a sound wave in the present invention.
Figure 2B:
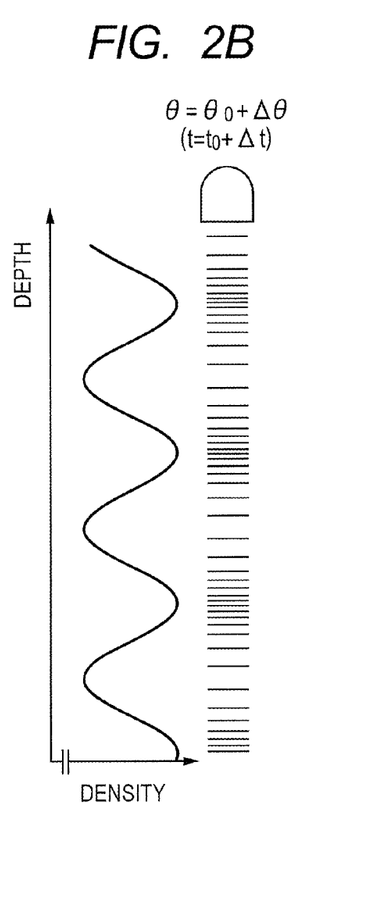

Subsequently, FIGS. 2A and 2B illustrate the states of a change in density of a sample measurement region before and after the sound wave irradiation. If a sample is irradiated with a sound wave which is a compressional wave, the density of each portion changes periodically along a sound wave traveling direction (See FIG. 2A). Since the phase at each point varies with time (See FIG. 2B), it is impossible to obtain a meaningful measured value only by performing the time-domain spectroscopic measurement while irradiating the sample with the sound wave. Therefore, when the irradiation sound wave (the sound wave generated from the sound wave generating section 1) has a predetermined phase angle (for example, a phase angle $\theta=\theta_0$ in FIG. 2A), measurement is made on the electromagnetic wave pulse with which the sample is irradiated and which reached the electromagnetic wave pulse detecting section 3. In this manner, the timing of measuring the electromagnetic wave pulse in conformity to the phase of the irradiation sound wave is set so that the measurement is able to be repeatedly performed under the same conditions, which is another feature of the present invention.

Figure 3A:
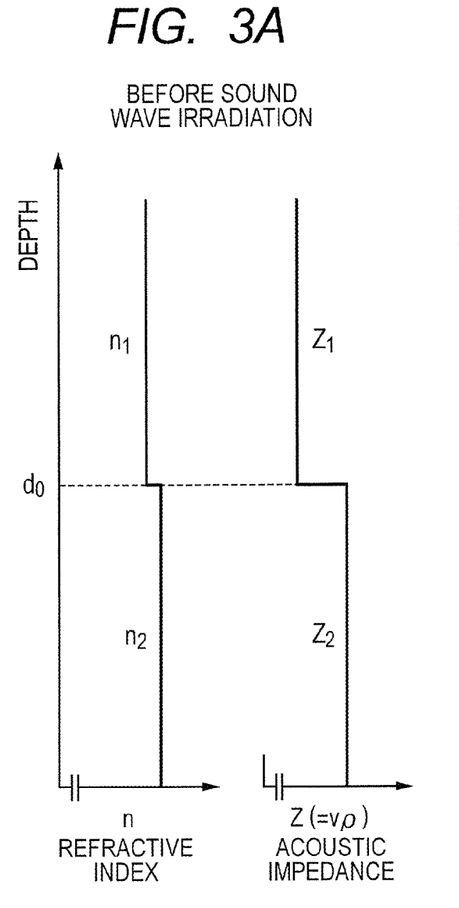
FIGS. 3A and 3B are diagrams illustrating the characteristics of a sample before and after sound wave irradiation in the present invention.
Figure 3B:
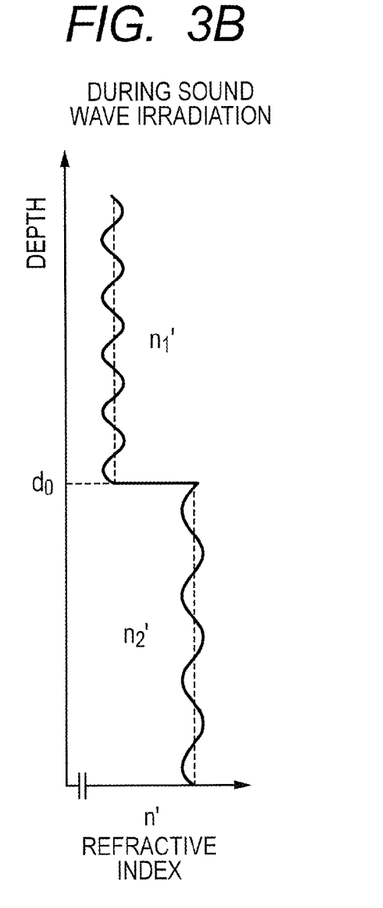

FIGS. 3A and 3B illustrate examples of the distribution of optical and acoustic characteristics of a sample measurement region before and after the sound wave irradiation. There is a boundary of composition at the depth $d_0$ of the sample, which causes discontinuity (step) in the refractive index n and the acoustic impedance Z as illustrated in FIG. 3A. Note here that the acoustic impedance Z is an amount given by a product $v\rho$ of the sonic speed v and the density $\rho$ in the sample. The electromagnetic wave pulse is affected by a disturbance in optical characteristics, while not relating directly to acoustic characteristics. There is a relationship, however, between the density $\rho$ and the refractive index n as represented by the so-called Lorentz-Lorenz formula described below, where M is the molecular weight, $\alpha$ is the polarizability per molecule, and $N_A$ is the Avogadro constant.

$$(n^2-1)/(n^2+2)\cdot M/\rho = (4\pi/3)\cdot N_A \cdot \alpha \tag{1}$$

The right-hand side and M are amounts specific to the sample, and therefore it is understood that a change in density of the sample associated with the sound wave irradiation increases or decreases the refractive index. A spatial period (wavelength) $\lambda$ is given by the ratio between the sonic speed v and the frequency f. Therefore, the refractive index in the sample measurement region during sound wave irradiation is modulated with a difference in the acoustic characteristics reflected. The state is illustrated in FIG. 3B. In the interface with the depth $d_0$, the waveform of the electromagnetic wave pulse is disturbed in a form of a difference in refractive index including the difference in modulation with the original difference in refractive index of the sample. This improves the contrast at the time of detecting the electromagnetic wave pulse.

Figure 4:
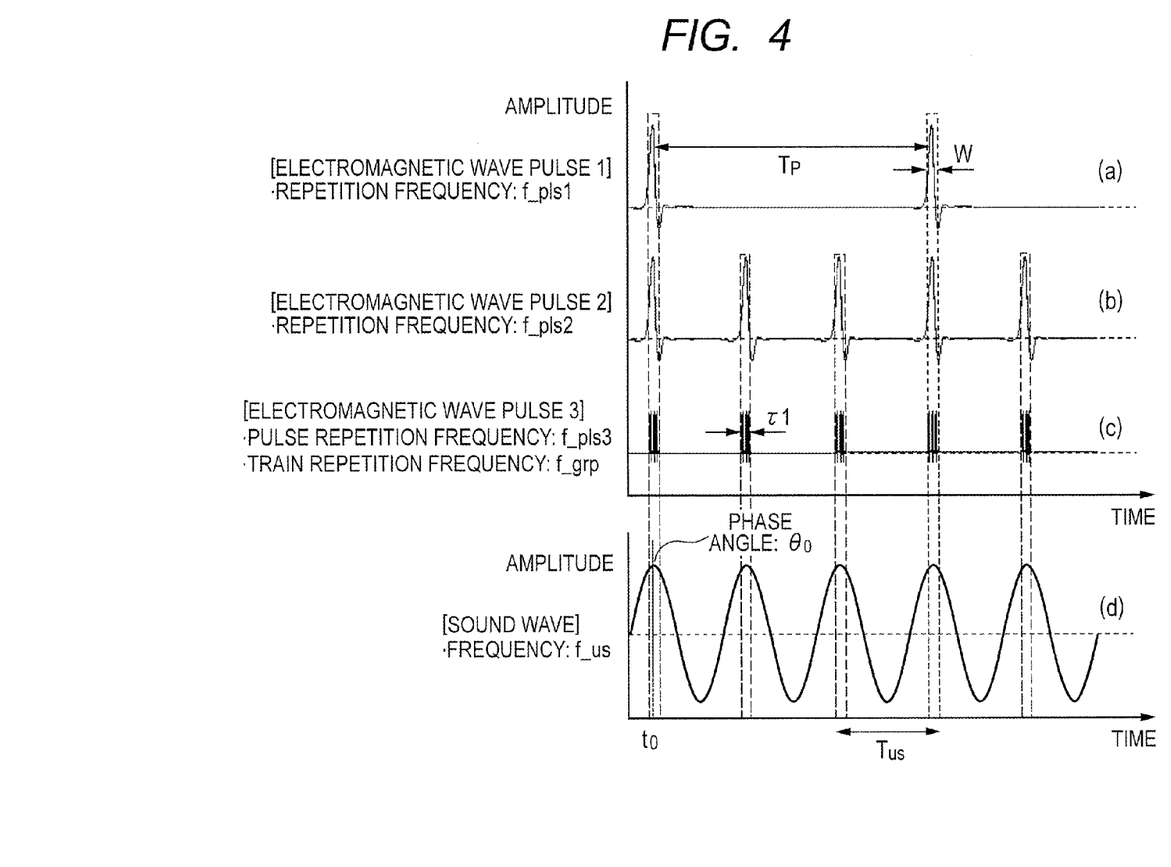
FIG. 4 is a diagram illustrating the irradiation timings of a sound wave and an electromagnetic wave pulse in the present invention.

Meanwhile, in order to measure an electromagnetic wave pulse when the sound wave has a predetermined phase angle as has been described as a feature of the present invention, the sound wave generating section 1, the electromagnetic wave pulse generating section 2, and the electromagnetic wave pulse detecting section 3 need to operate in cooperation with one another. For this purpose, for example, only when the timing at which the sound wave having the predetermined phase angle is present in the sample measurement region coincides with the irradiation timing of the electromagnetic wave pulse, the area is irradiated with the electromagnetic wave pulse. FIG. 4 illustrates an example of the timing at which the area is irradiated with both of the sound wave and the electromagnetic wave pulse. In FIG. 4, there are illustrated the waveforms of electromagnetic wave pulses (trains) during irradiation in (a) to (c) and the waveform of a sound wave in the sample measurement region in (d), with the horizontal axis representing time in each of (a) to (d). As illustrated in (d) of FIG. 4, the sample is assumed to be irradiated with the sound wave having a frequency f_us (period Tus).

In FIG. 4, (a) illustrates a state where the sample is irradiated with an extremely-short electromagnetic wave pulse at repetition frequency f_pls1 (electromagnetic wave pulse 1). The shorter the pulse width is, the more the resolution in the depth direction improves in the measurement. Also in order to increase the accuracy of measurement, the full width at half maximum W of the electromagnetic wave pulse is adapted to be at least one-tenth or less of the repetition period Tp. In addition, from the relationship with the irradiation ultrasonic wave, the full width at half maximum W of the electromagnetic wave pulse is adapted to be at least one-tenth or less of the period Tus of the sound wave.

Note here that the timing of the sound wave at detection is able to naturally coincide with the timing of the electromagnetic wave pulse by setting the repetition frequency f_pls1 of the electromagnetic wave pulse 1 to a fraction of a natural number of the frequency f_us of the sound wave.

$$m \cdot f_{pls1} = f_{us} \ (m: \text{natural number}) \quad (2)$$

Particularly, if the repetition frequency of the electromagnetic wave pulse is made equal to the frequency f_us of the sound wave (m=1), the number of measurements per period of the sound wave is able to be maximized so as to be efficient, by which improvement in the S/N ratio of the detected signal can also be expected. The state is illustrated in (b) of FIG. 4 (electromagnetic wave pulse 2). In the diagram, the repetition frequency f_pls2 of the electromagnetic wave pulse 2 is equal to the frequency f_us of the sound wave.

Moreover, when the repetition frequency of the electromagnetic wave pulse is sufficiently higher than the frequency of the sound wave, the sample may be irradiated with the subsequent (continuous) electromagnetic wave pulse train to perform the same detection as the above. The state is illustrated in (c) of FIG. 4. Here, the repetition frequency f_pls3 of the electromagnetic wave pulse 3 is assumed to be sufficiently, specifically ten times or more, higher than the frequency f_us of the sound wave. In addition, the time interval (duration) τ1 of the electromagnetic wave pulse train composed of continuous electromagnetic wave pulses is assumed to be sufficiently short in comparison with the period Tus of the sound wave. Specifically, the time of one-tenth or lower of the period Tus of the sound wave is secured. In this process, the repetition period Tp of the electromagnetic wave pulse is preferably 1/20 or less of the period Tus of the sound wave. If the timing at which the phase angle θ of the sound wave with which the sample measurement region is irradiated is $θ_0$ ($θ=θ_0$ is a timing at which the sample is required to be measured, the sample measurement region is irradiated with the electromagnetic wave pulse only for a time interval of the duration τ1 around the time (for example, $t_0$). As a result, in the irradiation electromagnetic wave pulse 3, a pulse train in which a pulse with a repetition frequency f_pls3 continues only for the time interval of the duration τ1 is repeated at frequency f_grp. Although the "train repetition frequency" f_grp is equal to the frequency f_us of the sound wave in (c) of FIG. 4, the former may be a fraction of a natural number of the latter in the same manner as in (a).

$$m \cdot f_{grp} = f_{us} \ (m: \text{natural number}) \quad (3)$$

Figure 5:
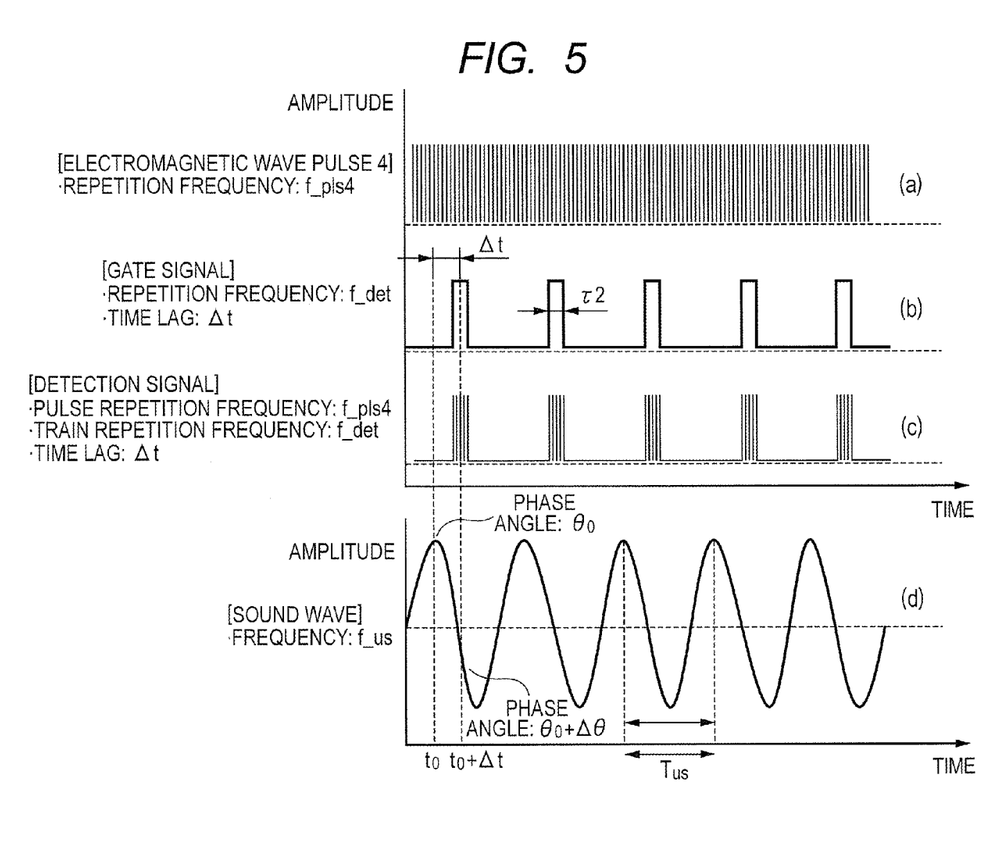
FIG. 5 is a diagram illustrating the detection timings of a sound wave and an electromagnetic wave pulse in the present invention.

Moreover, a limit may be imposed on the timing at which the electromagnetic wave pulse detecting section 3 detects the waveform of an electromagnetic wave pulse. The situation is illustrated in FIG. 5. In FIG. 5, graph (a) illustrates an electromagnetic wave pulse (repetition frequency f_pls4) with which the sample is irradiated and graph (b) illustrates a gate signal (repetition frequency f_det) representing the timing (gate time) at which the electromagnetic wave pulse detecting section 3 detects the waveform. Moreover, in FIG. 5, graph (c) illustrates a signal (train repetition frequency f_det) after the detection and graph (d) illustrates the waveform (frequency f_us) of the sound wave. The horizontal axis in each graph represents time. Here, it is assumed that $θ_0$ is the phase angle of the sound wave at time $t_0$, "$θ_0+Δθ$" is a phase angle after a lapse of time Δt, and a predetermined time interval (detection gate time τ) τ2 is sufficiently short in comparison with the period Tus of the sound wave. For example, the predetermined time interval is assumed to be a time interval of one-tenth or less of the period Tus of the sound wave. In the irradiation of the sample measurement region with the sound wave, the phase angle at the required measurement timing is assumed to be "$θ=θ_0+Δθ$." The electromagnetic wave pulse detecting section 3 detects an electromagnetic wave pulse only during a time interval of duration τ2 around the time when the sound wave has a phase angle "$θ_0+Δθ$" in the sample measurement region. As a result, the obtained signal reflects a repetition at a frequency f_det of a pulse train in which the electromagnetic wave pulse (repetition frequency f_pls4) having passed through the sample measurement region continues for the time interval of the duration τ2. In the same manner as for the above example, the train repetition frequency f_det may be a fraction of a natural number of the frequency f_us of the sound wave.

The foregoing has described a method of controlling the timing of irradiation with the electromagnetic wave pulse and a method of controlling the timing of selecting the electromagnetic wave pulse to be measured. Naturally, a combination of both methods may be employed. This case enables a signal to be detected more sensitively than in a case of using only one of the methods. In addition, the description has been made assuming that the sample is continuously irradiated with the sound wave, the sample may be intermittently irradiated with the sound wave. Note that, however, the sound wave needs to be generated in such a way that the same phase angle is made every time at the timing of irradiation and detection of the electromagnetic wave pulse.

Hereinafter, more specific examples will be described in more detail with reference to appended drawings.

Example 1

Figure 6:
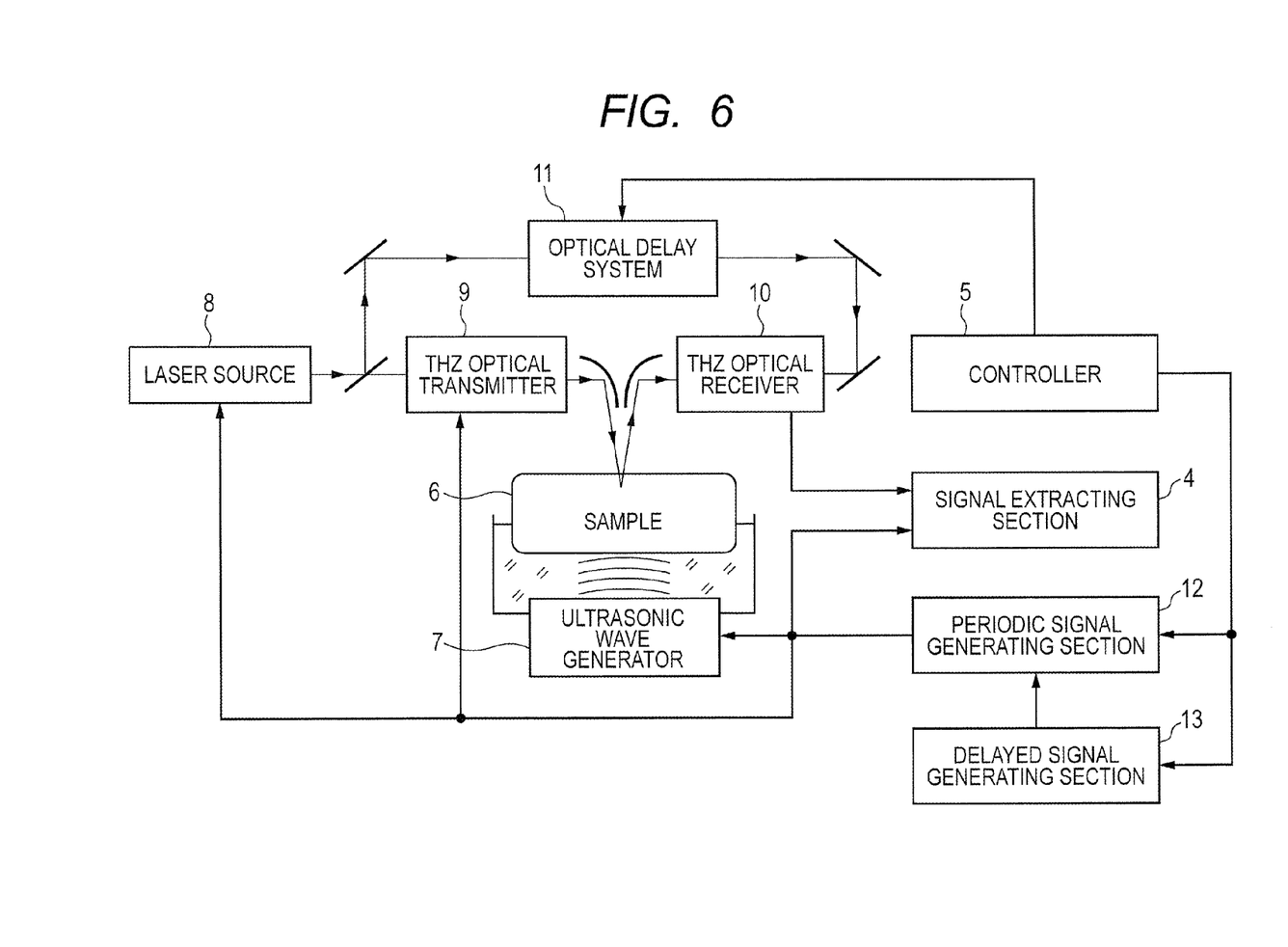
FIG. 6 is a block diagram illustrating a basic configuration in a first example of the present invention.

A first example of the present invention will be described in detail by using FIG. 6. In this example, an electromagnetic wave pulse in the THz band (an electromagnetic wave including one of frequencies in a range of 30 GHz to 30 THz) is emitted from the front-face side of the sample 6 and an ultrasonic wave is emitted from the rear-face side of the sample 6. An ultrasonic wave generator 7 emits an ultrasonic wave having a predetermined frequency toward the sample 6 on the basis of a signal from the periodic signal generating section 12. For the ultrasonic wave generator 7, there is used, for example, an ultrasonic transducer having an electro-acoustic conversion function, which is mainly composed of a piezoelectric device. The ultrasonic wave generator 7 is in close contact with the sample 6 or a space therebetween is filled with an impedance matching material simply illustrated in FIG. 6, so that the ultrasonic wave is efficiently transmitted to the sample 6 in the entire configuration.

Here, for the periodic signal generating section 12, an existing high-frequency oscillator is able to be used. For the oscillating frequency, an optimal value may be selected according to the sample 6. If the target is a biological body, several MHz such as, for example, MHz is preferably used. Moreover, the oscillating frequency and the presence or absence of an output are controlled by a signal from a controller 5 and the phase angle of oscillation is controlled by a signal from the delayed signal generating section 13. A laser source 8 is a light source which generates ultrashort pulsed light periodically. For example, there is preferably used a mode-locked Ti:sapphire laser, a fiber laser, or the like which outputs femtosecond-order ultrashort pulsed light with a repetition frequency of approx. 80 MHz. The ultrashort pulsed light is divided in half by a beam splitter or the like and one of the divided light beams impinges on a THz optical transmitter 9. The THz optical transmitter 9 is mainly composed of a photoconductive device or a nonlinear optical crystal using, for example, low temperature grown GaAs and generates an electromagnetic wave pulse in the terahertz band (hereinafter, also referred to as a terahertz pulse) along with the impinging of the ultrashort pulsed light, which is a pump light. A typical example of a terahertz pulse has a bandwidth of 7 THz and a pulse width of 300 fs. The repetition frequency of a terahertz pulse is described later.

The terahertz pulses are collected by a dedicated optical system a part of which is illustrated and are emitted to the sample measurement region modulated in density by the ultrasonic wave irradiation. For the light collecting optical system, an off-axis paraboloidal mirror or the like is preferably used. The terahertz pulses reflected on the respective portions of the sample including measurement region are collected by another optical system and impinge on a THz optical receiver 10. The THz optical receiver 10, which is configured on the basis of, for example, the aforementioned photoconductive device, detects the amplitude of the impinging terahertz pulse in conformity with the timing at which a probe light impinges on the THz optical receiver 10. The details of the timing are also described later. Here, the probe light impinging on the THz optical receiver 10 is the other of the aforementioned halved outputs from the laser source 8 which has passed through an optical delay system 11. The optical delay system 11 is a mechanism which controls the optical path length of a passing light according to an external signal and is able to be composed of, for example, a combination of an existing folding optical system and a moving stage.

In this example, the controller 5 controls the optical delay system 11, the periodic signal generating section 12, and the delayed signal generating section 13 and causes them to operate in cooperation with each other to generate, emit, and detect an ultrasonic wave and a terahertz pulse. Specifically, first, the controller 5 controls signals from the periodic signal generating section 12 and the delayed signal generating section 13 and determines the frequency of the ultrasonic wave to be emitted and the phase angle at the detection. The signal from the periodic signal generating section 12 is supplied to the laser source 8 and to the THz optical transmitter 9 to determine the repetition frequency of the terahertz pulse to be emitted. Moreover, a signal extracting section 4 extracts or detects only components synchronized with the signal from the periodic signal generating section 12 out of the reflected terahertz pulses which have been detected. For this process, for example, a commercially available lock-in amplifier may be used. Since a signal proportionate to the amplitude of the terahertz pulse is obtained as an output, a desired waveform of the terahertz pulse is obtained by sweeping by the optical path length by using the optical delay system 11.

The following describes the timing control of the irradiation and detection of the ultrasonic wave and the terahertz pulse which is a feature of the present invention. The configuration on the side of the terahertz pulse irradiation is described, first. A typical frequency of the laser source 8 used for a pump light or a probe light is approx. 80 MHz, which is one to three digits higher than the frequency of the ultrasonic wave used within a range of several tens kHz to several MHz. If an ultrasonic wave with the frequency of 1 MHz is generated, the ratio is approx. 80 times higher than the ultrasonic wave. Therefore, an optical chopper is embedded into the THz optical transmitter 9, a pump light pulse is extracted in conformity with the timing of the ultrasonic wave (frequency f_us=1 MHz), and the pump light pulse impinges on the photoconductive device and the nonlinear optical crystal. The optical chopper may have a rotatable blade or may be an application of an electro-optic device. Moreover, in the case where a bias voltage needs to be applied at an occurrence of a terahertz pulse like a photoconductive device, the bias voltage may be modulated. Taking FIG. 4 for example, the chopping frequency or the modulation frequency of the optical chopper is set to a repetition frequency f_pls1=250 kHz (a), f_pls2=1 MHz (b), or f_grp=1 MHz (c).

As the laser source 8, a light source capable of externally controlling the repetition frequency of the output optical pulse may be used. The configuration of this type of light source is already known and the light source is commercially available. In this case, the light source controls the repetition frequency (80 MHz) of the optical pulse so as to be synchronized with the frequency of a signal from the periodic signal generating section 12, in other words, a natural number multiple or a fraction of a natural number of the frequency (1 MHz) of the ultrasonic wave. Moreover, if the laser source 8 is sufficiently stable, the controller 5 may be adapted to directly control the repetition frequency of the optical pulse (this configuration is not illustrated). In this configuration, the entire accuracy is increased by dividing the repetition frequency of the optical pulse and synchronizing the output signal of the periodic signal generating section 12 with the divided repetition frequency.

The same configuration may be used on the side of the detection of the terahertz pulse. For example, the optical chopper is embedded into the THz optical receiver 10, only a probe light conforming to the timing of the frequency f_us of the ultrasonic wave is extracted, and the probe light impinges on the receiving device or crystal. Specifically, taking FIG. 5 for example, a chopper window (opening) is configured so that the "H (ON)" state of the gate signal in (b) corresponds to the time domain in which the probe light passes through the chopper window. If a photoconductive device is used for the THz optical receiver 10, a bias voltage may be modulated. In this configuration, a bias signal corresponding to the gate signal in (b) is applied to the photoconductive device.

Figure 7:
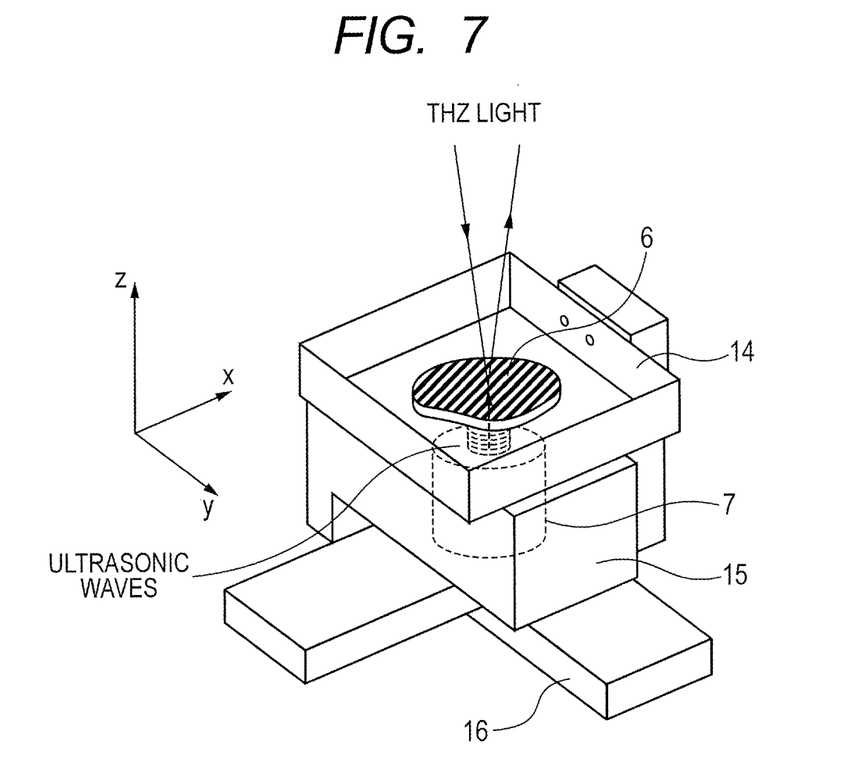
FIG. 7 is a diagram illustrating an illustrative embodiment of a configuration in the first example of the present invention.

Subsequently, a specific configuration of this example will be described by using FIG. 7. To know the characteristic distribution of the sample, it is necessary to perform sequential measurement while changing the measurement region irradiated with the ultrasonic wave or the terahertz pulse. Therefore, the configuration is made so that the measurement region of the sample is movable in directions substantially perpendicular to the axis in which the terahertz pulse is emitted (in the X and Y directions in FIG. 7). A sample holder 14 holds and fixes the sample 6 to the bottom of the sample holder. In the measurement, the terahertz pulse is emitted from above to the sample 6 by a THz optical transmitter, which is not illustrated. The reflected light is collected and detected by the THz optical transmitter, which is not illustrated. Meanwhile, a sample stage 15 is fixed to a floor surface and holds the ultrasonic wave generator 7 inside. In the measurement, the ultrasonic wave generator 7 emits the ultrasonic wave from the rear-face side of the sample 6 via the sample holder 14. Preferably, the space between the sample holder 14 and the sample 6 is filled with an appropriate matching material such as water.

In addition, an XY stage 16 is fixed at the lower part (the Y stage in FIG. 7) to the floor and at the upper part (the X stage) to the sample holder 14. Note here that the sample holder 14 is placed on the sample stage 15, but not fixed thereto. Similarly, the XY stage 16 and the bottom face of the sample stage 15 are adapted so as not to interfere with each other. As a result, the XY stage 16 is able to sweep the position in the X and Y directions of the sample holder 14 and thus the sample 6 according to the signal from the controller 5 (See FIG. 6).

In the measurement, the sample 6 is irradiated with the ultrasonic wave from below of the sample and with the terahertz pulse from above of the sample while sweeping the sample 6 in the X and Y directions and the terahertz pulse reflected on the sample 6 is measured. The waveform of the pulse includes information on the sample depth direction (Z direction) at each point. A three-dimensional characteristic distribution of the sample, namely a so-called tomographic image is able to be obtained by collecting and organizing the information. In this example, further it is also possible to obtain fourth-dimensional information by performing the measurement while changing the phase angle ("$\theta_0+\Delta\theta$" in FIG. 5) of the ultrasonic wave. Sweeping the phase angle of the ultrasonic wave is equivalent to vertically moving the positions of the nodes and antinodes of the density and thus the refractive index in the inside of the sample. In other words, it is possible to sweep the depth position in which the terahertz pulse is reflected. Also in the case where a reflected signal is not obtained without ultrasonic wave irradiation, information on the inside of the sample is obtained advantageously.

Although the optical system is fixed and the sample 6 is moved in the above description, the optical system may be moved in another configuration. In this configuration, the sample holder 14 is fixed to the floor and not moved during measurement. Moreover, the sample stage 15 including the ultrasonic wave generator 7 and the terahertz pulse optical system are attached to the XY stage 16. This arrangement is effective in the case where it is difficult to move the sample. As described hereinabove, there is achieved an image forming apparatus which includes a mechanism for scanning the position of a predetermined area of a sample in an electromagnetic wave pulse measuring device of the present invention, wherein an internal cross-sectional image or a stereoscopic image of sample characteristics is displayed on the basis of a result of measuring the waveform of the electromagnetic wave pulse while scanning the position of a predetermined area of the sample.

Example 2

A second example of the present invention will be described below by using FIG. 8. Most of the configuration and the operations of the respective parts are the same as in the example 1. Therefore, only the part in the vicinity of the sample, which is different from the example 1, is described in detail below. This example is characterized by that the ultrasonic wave generator 7 irradiates the measurement region of the sample 6 with an ultrasonic wave so as to converge to the measurement region.

In the ultrasonic wave generator 7, for example, a plurality of ultrasonic transducers each with an acoustic lens attached to the tip portion are disposed with the line of fire inclined so that the focal point coincides with the sample measurement region. In this specification, a biological body is assumed to be the sample 6 to describe the situation of measuring the vicinity of the skin on the under side of the forearm (the palm side of the hand). The ultrasonic wave generator 7 is pushed against the upper side of the forearm (the back side of the hand) or the lateral side thereof to prevent an interference with the optical system for a terahertz pulse. The contact position and the irradiation direction of the ultrasonic wave are adjusted in advance so that the focal point comes to a region required to be measured. Although FIG. 8 illustrates a configuration in which only one ultrasonic wave generator 7 is used, a plurality of ultrasonic wave generators 7 may be used. Note that, however, the frequency and the focal position of the ultrasonic wave in each ultrasonic wave generator need to coincide with each other in the configuration.

Figure 8:
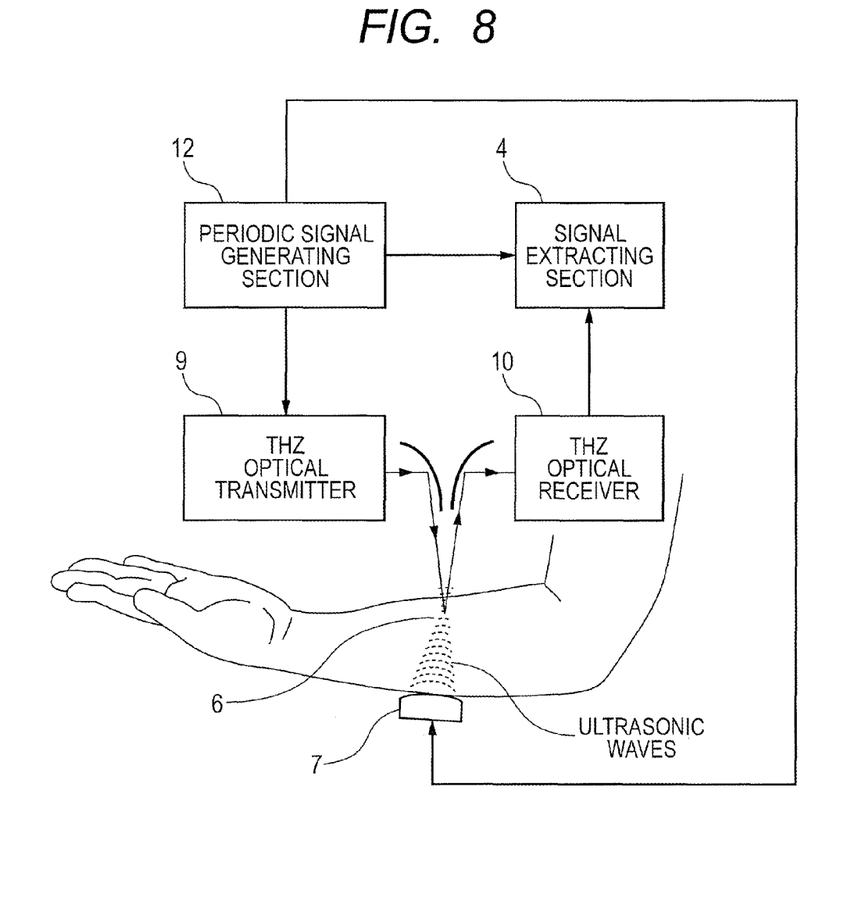
FIG. 8 is a block diagram illustrating the configuration of a main part of a second example of the present invention.
Figure 9A:
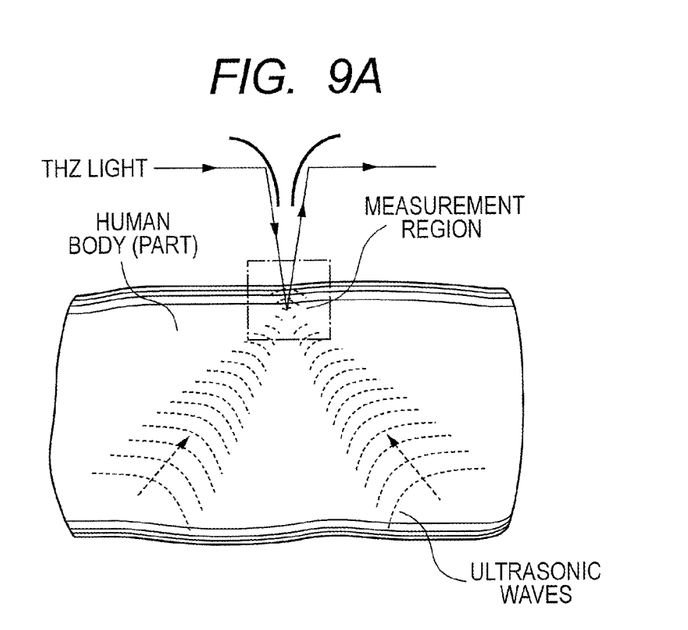
FIGS. 9A and 9B are diagrams illustrating the states of a measurement region in the second example of the present invention.
Figure 9B:
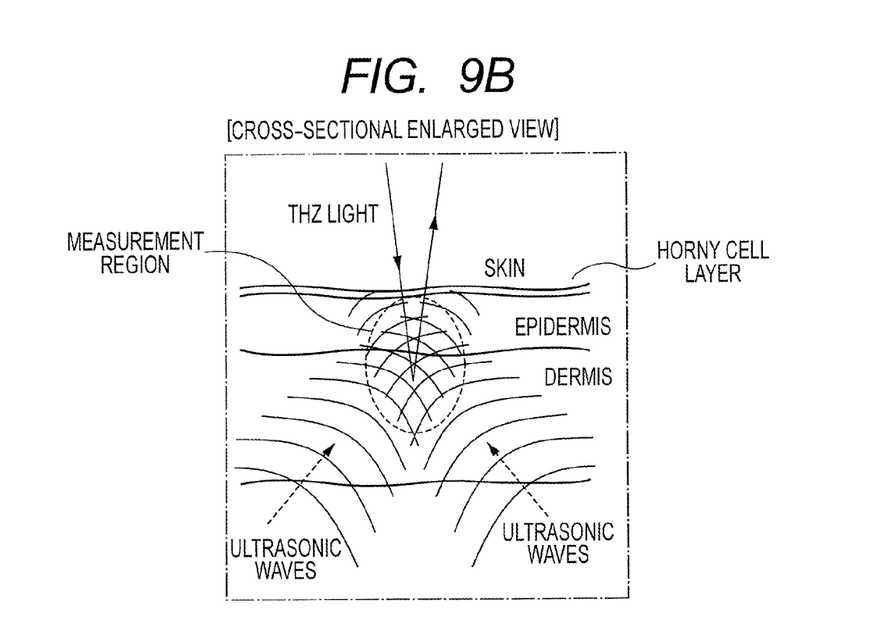

FIGS. 9A and 9B illustrate the vicinity of the sample measurement region in FIG. 8. FIG. 9A illustrates a state in which a part of the forearm is irradiated with the terahertz pulse and the ultrasonic waves. Two ultrasonic wave generators 7 disposed outside the range of the diagram generate the ultrasonic waves so as to narrow the ultrasonic waves toward the above measurement region. FIG. 9B is a cross-sectional enlarged view of the vicinity of the measurement region. Human skin has a structure of layers called a horny cell layer, an epidermis, and a dermis in order from the surface. Their thicknesses are on the order of 20 µm, 200 µm, and 2 mm, respectively. These thicknesses largely vary according to a region of the body and depend on the health condition. For example, aging and ultraviolet light contribute to a decrease in the epidermis thickness, while stimulus and bacterial infection contribute to an increase in the epidermis thickness. Moreover, inflammation may affect the interface of each layer such as an occurrence of edema, disordering the regularity of the concavity and the convexity between the epidermis and the dermis (papillary layer), or the like. Accordingly, it is important in diagnosis to know the thicknesses of the respective layers of the skin and the state of the interface. Measurement with a terahertz pulse is an effective measure therefor since information on the state under the skin is available without damaging the biological body by penetrating into the body.

Meanwhile, apparently it is important to acquire information on the composition as well as information on the structure to know the health condition of the skin. Also in this respect, the waveform measurement with a terahertz pulse is effective. For example, the respective layers of the skin contain a large amount of moisture, and the distribution and information on the increase and decrease of the moisture give a lot of suggestions to diagnoses. The electromagnetic wave in the terahertz band is absorbed well by water and therefore is sensitive to a change in the percentage of moisture content. Therefore, the electromagnetic wave is applicable to detecting the presence or absence of inflammation and an abnormal tissue such as a tumor (there is a difference in the percentage of moisture content between a normal skin tissue and an abnormal tissue such as a tumor). Moreover, it is also possible to grasp temporal variations in the degree of penetration of a transdermal drug by focusing attention on the absorption spectrum of a specific wavelength of the drug, utilizing the advantage of the in-vivo measurement.

While the above is the description of a diagnostic method based on the optical characteristics of a body tissue, differences in acoustic characteristics are additionally used for the detection in the present invention. The sonic speed in a biological body reflects the elasticity of tissues, in other words, a difference in coupling strength between homologous or heterologous cells, or the state of an extracellular matrix such as collagen. Not only between different layers, but also within the same layer, a region where an inflammation or a tumor occurs and an area therearound have different acoustic characteristics from those of a normal region. This is because there is a difference in the coupling strength between cells or a matrix state. In the present invention, the difference in the acoustic characteristics is reflected on the optical characteristics by the ultrasonic wave irradiation, and therefore a difference between tissues is able to be detected more sensitively than the measurement with only the terahertz pulse.

Moreover, according to the configuration of this example, the strength of the ultrasonic wave increases only in the vicinity of the sample measurement region, and therefore the contrast in the measurement further increases. Further, if the ultrasonic wave is sufficiently focused, a reflected pulse is obtained from a region where any reflected pulse is not obtained before the irradiation. In addition, the axis of the irradiation direction of each ultrasonic wave deviates from that of the terahertz pulse as illustrated in FIGS. 9A and 9B, thereby achieving effects of suppressing the density modulation, which is caused by ultrasonic waves, in areas other than the measurement region of the sample and reducing unnecessary scattering of the terahertz pulse. Moreover, this example has another advantage that it is possible to irradiate the sample with the ultrasonic waves with avoiding an optical system for terahertz pulse irradiation which requires a relatively wide space.

Example 3

Figure 10:
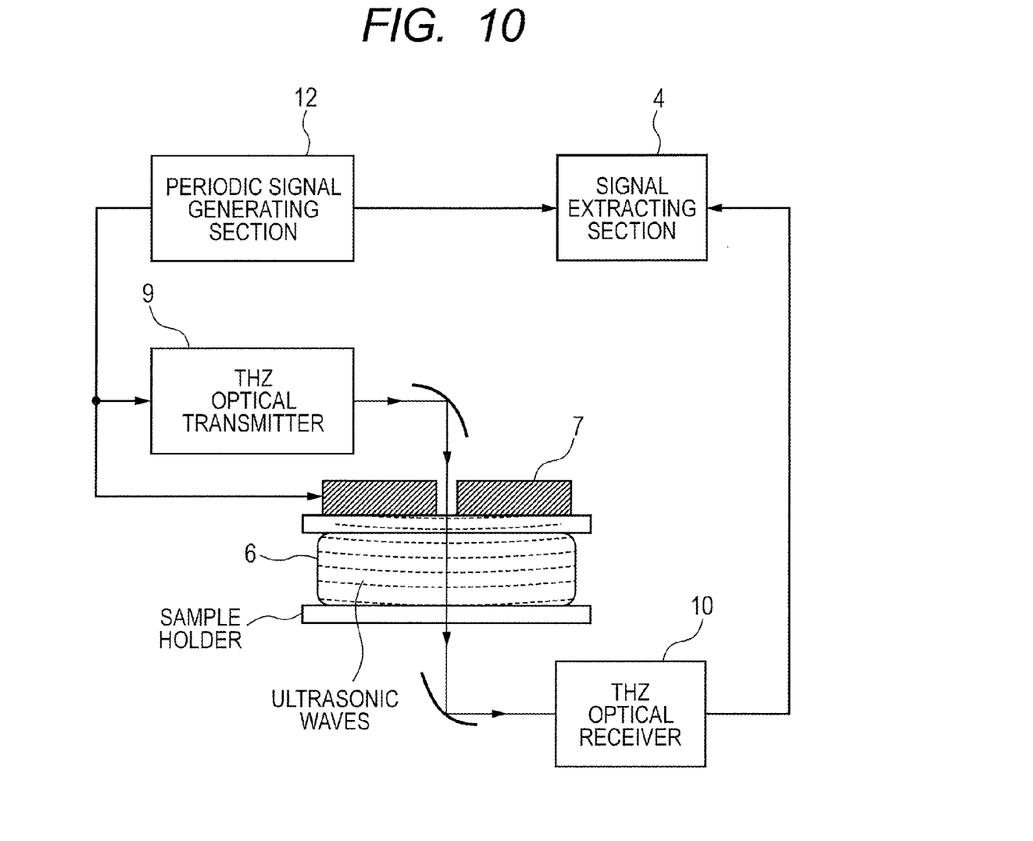
FIG. 10 is a block diagram illustrating the configuration of a main part in a third example of the present invention.

A third example of the present invention will be described by using FIG. 10. Also in this example, most of the configuration and the operations of the respective parts are the same as in the example 1. Therefore, the part in the vicinity of the sample, which is different from the example 1, is described in detail below. This example is characterized by that the ultrasonic wave generator 7 and the THz optical transmitter 9 are configured to emit the ultrasonic wave and the terahertz pulse coaxially with each other and in the same direction. There is provided a transmissive system wherein the terahertz pulse impinges on the surface of the sample and passes through to the rear of the sample. Accordingly, the ultrasonic wave generator 7 is provided with an opening, so that the terahertz pulse is able to pass through the opening. The sample 6 is held with being in close contact with the inside of the sample holder formed of a material through which the terahertz pulse passes. The sample holder is also in contact with the ultrasonic wave generator 7 and functions as an impedance matching material.

This example has an advantage that an optical adjustment is easy since the lines of fire of the ultrasonic wave and the terahertz pulse are coaxial with each other. Moreover, the example has an effect of an increase in contrast caused by the ultrasonic wave irradiation also in the measurement of a sample through which the terahertz pulse easily passes.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-061391, filed Mar. 19, 2012, which is hereby incorporated by reference herein in its entirety.

The invention claimed is:

1. An electromagnetic wave pulse measuring device for acquiring information on a sample using time-domain spectroscopy comprising:
    an elastic vibration wave generating section which irradiates the sample with an elastic vibration wave;
    an electromagnetic wave pulse generating section which irradiates the sample with an electromagnetic wave pulse; and
    an electromagnetic wave pulse detecting section which measures a time waveform of the electromagnetic wave pulse modulated by the sample,
    wherein the electromagnetic wave pulse detecting section and the elastic vibration wave generating section are configured such that the electromagnetic wave pulse detecting section measures the time waveform of the electromagnetic wave pulse at a timing when the elastic vibration wave generating section generates the elastic vibration wave with a phase angle of a predetermined value.

2. The electromagnetic wave pulse measuring device according to claim 1, wherein a repetition frequency of the electromagnetic wave pulse with which the sample is irradiated is a fraction of a natural number of the frequency of the elastic vibration wave.

3. The electromagnetic wave pulse measuring device according to claim 1, wherein the sample is repeatedly irradiated with an electromagnetic wave pulse train including continuous electromagnetic wave pulses and a repetition frequency of the electromagnetic wave pulse train is a fraction of a natural number of the frequency of the elastic vibration wave.

4. The electromagnetic wave pulse measuring device according to claim 3, wherein a duration $\tau$ of the electromagnetic wave pulse train is one-tenth or less of a period Tus of the elastic vibration wave and a repetition period Tp of the continuous electromagnetic wave pulses is one-twentieth or less of the period Tus of the elastic vibration wave.

5. The electromagnetic wave pulse measuring device according to claim 1, wherein the electromagnetic wave pulse detecting section includes a signal extracting section which detects waves in synchronization with the frequency of the elastic vibration wave.

6. The electromagnetic wave pulse measuring device according to claim 5, wherein gate time $\tau$ used when the signal extracting section detects the electromagnetic wave pulse is one-tenth or less of the period Tus of the elastic vibration wave and the repetition period Tp of the electromagnetic wave pulse is one-twentieth or less of the period Tus of the elastic vibration wave.

7. The electromagnetic wave pulse measuring device according to claim 1, wherein the elastic vibration wave generating section irradiates the sample with the elastic vibration wave so that the elastic vibration wave converges to the predetermined area.

8. The electromagnetic wave pulse measuring device according to claim 1, further comprising a controller which controls a predetermined value of the phase angle of the elastic vibration wave when the elastic vibration wave generating section emits the elastic vibration wave.

9. The electromagnetic wave pulse measuring device according to claim 1, wherein the electromagnetic wave includes any one of the frequencies in a range of 30 GHz to 30 THz.

10. The electromagnetic wave pulse measuring device according to claim 1, wherein a full width at half maximum of the electromagnetic wave pulse is one-tenth or less of the repetition period Tp of the electromagnetic wave pulse.

11. An image forming apparatus comprising:
the electromagnetic wave pulse measuring device according to claim 1; and
a mechanism which scans the sample in the electromagnetic wave pulse measuring device,
wherein an internal cross-sectional image or a stereoscopic image of sample characteristics on the basis of a result of measuring the waveform of the electromagnetic wave pulse while scanning the sample.

12. An electromagnetic wave pulse measuring method for acquiring information on a sample using time-domain spectroscopy comprising the steps of:
emitting an elastic vibration wave to the sample;
irradiating the sample with an electromagnetic wave pulse; and
measuring a time waveform of the electromagnetic wave pulse modulated by the sample, wherein, in the step of measuring a time waveform of the electromagnetic wave pulse, the time waveform of the electromagnetic wave pulse is measured at a timing when the elastic vibration wave is emitted with a phase angle of a predetermined value in the step of emitting the elastic vibration wave.

* * * * *